United States Patent [19]
Taranowski

[11] Patent Number: 5,303,037
[45] Date of Patent: Apr. 12, 1994

[54] COLOR SENSOR ILLUMINATION SOURCE EMPLOYING A LIGHTPIPE AND MULTIPLE LEDS

[75] Inventor: Michael G. Taranowski, Milwaukee, Wis.

[73] Assignee: Eaton Corporation, Cleveland, Ohio

[21] Appl. No.: 840,477

[22] Filed: Feb. 24, 1992

[51] Int. Cl.$^5$ .................................. G01N 21/27
[52] U.S. Cl. .................... 356/406; 250/226; 356/402
[58] Field of Search ............... 356/402–411, 356/445–448; 359/618, 629, 639–640; 250/226

[56] References Cited
U.S. PATENT DOCUMENTS

| | | | |
|---|---|---|---|
| 4,131,367 | 12/1978 | French et al. | 356/405 |
| 4,464,054 | 8/1984 | Karras et al. | 356/406 |
| 4,518,259 | 5/1985 | Ward | 356/446 |
| 4,626,679 | 12/1986 | Kuwayama et al. | 200/227 |
| 4,644,153 | 2/1987 | Ida | 250/225 |
| 4,815,816 | 3/1989 | Schneider | 250/227 X |
| 4,838,697 | 6/1989 | Kurandt | 356/406 |
| 4,917,500 | 4/1990 | Lugos | 356/406 |
| 5,011,261 | 4/1991 | Gordon | 358/75 X |

OTHER PUBLICATIONS

University Physics, 4th Edition, Sears et al, pp. 540–541, 1970.

Primary Examiner—Vincent P. McGraw
Assistant Examiner—K. P. Hantis
Attorney, Agent, or Firm—L. H. Uthoff

[57] ABSTRACT

A light transmitting source for a color sensor utilizes a plurality of light emitting diodes emitting light in a predetermined narrow range of wavelength whose emitted light strikes a surface of a lightpipe whereupon the light is reflected and refracted and directed to a common reflection point and where each emitted light is attenuated by the reflection and refraction a desired amount and directed to illuminate an object whose color is to be measured.

12 Claims, 3 Drawing Sheets

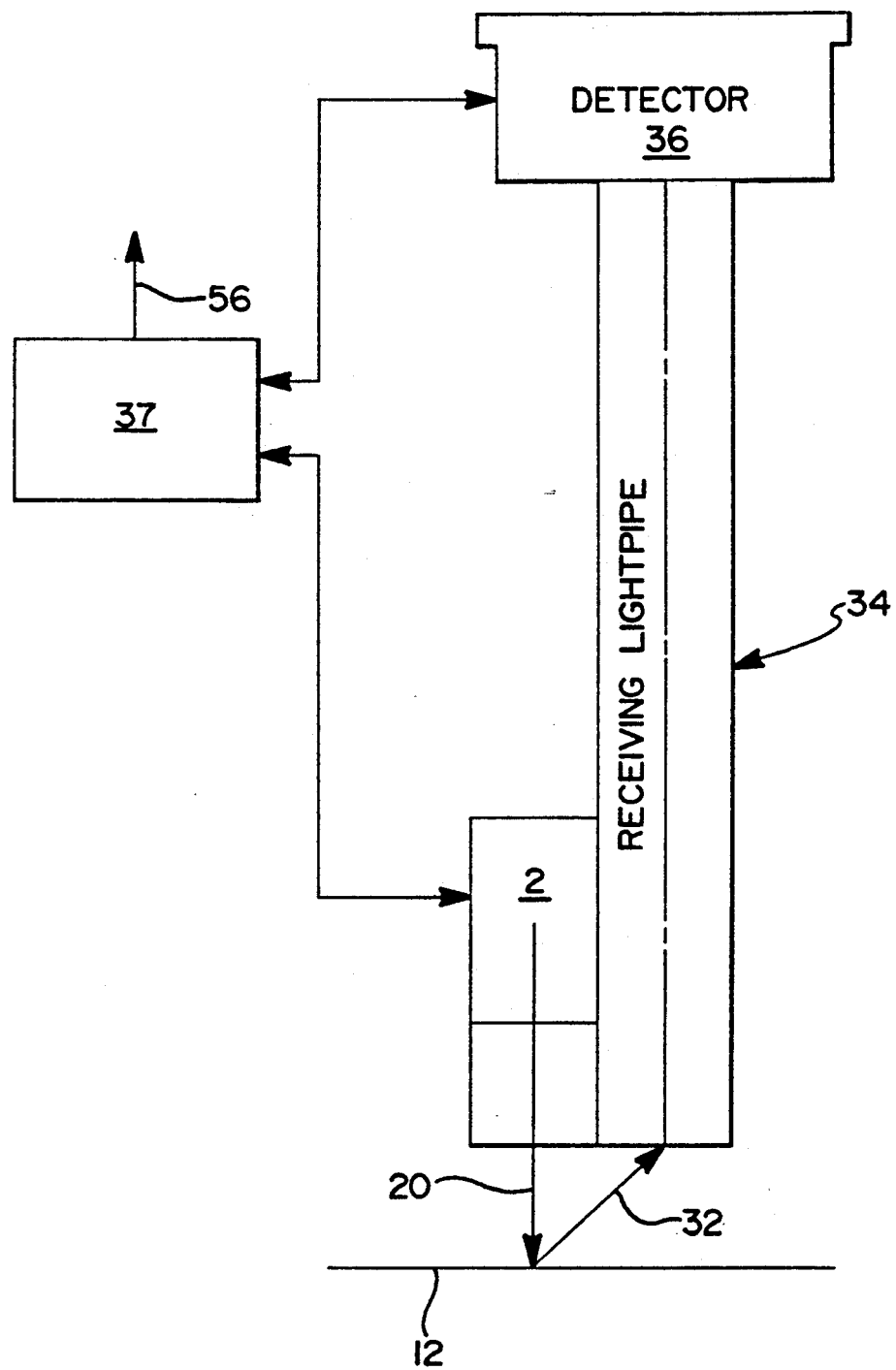

COLOR SENSOR ILLUMINATION SOURCE EMPLOYING A LIGHTPIPE AND MULTIPLE LEDS

RELATED APPLICATIONS

This application is related to 1) application U.S. Ser. No. 07/727,730 entitled "Color Sensor Employing Optical Fiber Bundles with Varied Diameters" filed on Jul. 10, 1991, now U.S. Pat. No. 5,229,841 and 2) application U.S. Ser. No. 07/674,247 entitled "Electric Color Sensor" filed on Mar. 25, 1991, now U.S. Pat. No. 5,150,174 both of which are assigned to the same assignee, Eaton Corporation, as this application.

FIELD OF THE INVENTION

The present invention relates to a color sensor for the recognition of objects and surfaces that are at least partially colored. More specifically, the present invention relates to a color sensor illumination source which employs a multiplicity of light emitting diodes emitting light within a frequency band of discrete chromaticity which impinges on the outer surface of a lightpipe having a geometry such that the incident lightwaves are reflected and refracted so as to create an output light having the desired amplitude and direction to illuminate an object whose color is to be measured.

DESCRIPTION OF THE PRIOR ART

Color is a very important factor in maintaining the overall quality of food products and manufactured goods. Because the color of a product is often equated to quality, it is highly desirable to be able to control the product processing based on a color measurement to maintain consistency and adhere to specified product standards. By incorporating a color sensing system on the production line, more products can be monitored than would be recognized by off line measurement techniques. Currently available color sensor technology has a number of limitations, not the least of which are the size and expense of the color illumination source, receiver and post-processing unit.

In conventional color recognition devices, the object whose colors is to be measured is illuminated with white light from a light source such as a halogen lamp. Reflected light is then decomposed by means of lenses and standard color filters into the primary colors of red, green and blue. The intensity of the individual color components is then converted into electrical signals by photo detectors which are connected to a receiving amplifier. The amplified electrical signals are then fed into a central processing system for a color determination and output representative thereof.

It is also known to use a light output of a plurality of light emitting diodes (LEDs) which are directed (or the emitted light is carried by optical fibers) so that their emitted light is reflected off of the object whose color is to be measured. The reflected light is then carried back to a photo sensitive device contained in an electronic processing unit where the reflected light output is measured and converted into an electrical signal.

U.S. Pat. No. 4,917,500, the disclosure of which is hereby incorporated by reference, describes a color sensor system where the light emitted from a plurality of LEDs is directed and conducted to an object whose color is to be measured by a transmitting optical wave guide made up of a bundle of optical fibers. The reflected light is then conducted back to a light receiver by a receiving optical wave guide to a photo semiconductor. The output of the light receiver is inputted to a central processing system where a representative signal of the object's color is generated as an output for interpretation and use in controlling a manufacturing process. The disadvantage to this type of system is the expense and packaging associated with the use of several optical fiber bundles and the optical fiber head and the difficulties associated with joining the optical fibers to the light transmitting LEDs.

In most manufacturing operations, space is at a premium and most of the prior art color sensors require that the light source and the receiver be in close proximity to the manufactured object whose color is to be measured which limits their use. As a result, color sensors are typically employed in the manufacturing environment on an off line basis rather than for quality control as the product moves down the processing line.

Fiber optics can be used to eliminate the need for the light source and the receiver to be in close proximity to the object, but their use increases the expense of the system. It is highly desirable to minimize the packaging space necessary to install a color sensor system for use on a process line in a manufacturing plant environment. Also, for obvious reasons, it would be desirable to minimize the cost of the color sensor system, especially where many units are required.

Another limitation with prior art color sensor systems is that the illuminating light exits the transmitting medium at different angles according to the positioning of the LED relative to the target. The result is that the response of the color sensor is different for each LED color depending on the distance from the LED to the target. This results in increased variability and inaccuracy.

SUMMARY OF THE INVENTION

The present invention provides a new and improved compact LED-based light source for illuminating a target whose color is to be measured where the light impinges the target at the same angle for each color. In this manner, the variability in output for each LED as the distance from the LED to the target is varied is minimized so that a proper balance of the illuminating colors is maintained. The result is that the color sensor has a decreased sensitivity and variability due to the distance from the illuminating LED to the target which is quite important in a manufacturing environment.

This balancing of light output power and the common light output angle is obtained with the use of a lightpipe. The faces of the lightpipe are positioned relative to one another and to the LED whose output light is reflected and refracted thereby, to direct the light output to a final transmitting surface for direction to the target. By calculating the incident angle of the light to a reflecting and refracting surface and using the losses inherent as a result, the output of the blue, green, and red LEDs can be balanced to yield a mixed light output with proper amplitude of each of the colors. Also, the reflecting and refracting surfaces of the lightpipe act as a means to cause the LED generated light to exit on the same axis. This produces an illuminating light quality such that reflection off of a Kodak White card produces the desired reflected light output to a receiver. The present invention also provides a low cost method of producing an illuminating light exiting at a given angle towards a target requiring a minimum of packaging space.

These and other features and advantages of the present invention will become apparent upon reading the following specification, which, along with the patent drawings, describes and discloses a preferred embodiment of the invention in detail.

A detailed description of the embodiment of the invention makes reference to the accompanying drawings.

BRIEF DESCRIPTION OF THE DRAWINGS

FIG. 2 is an elevational view of the illumination source of the present invention as shown in FIG. 1 mounted to a receiving lightpipe which is connected to a detector;

DETAILED DESCRIPTION OF THE PREFERRED EMBODIMENT OF THE INVENTION

Figure 1:
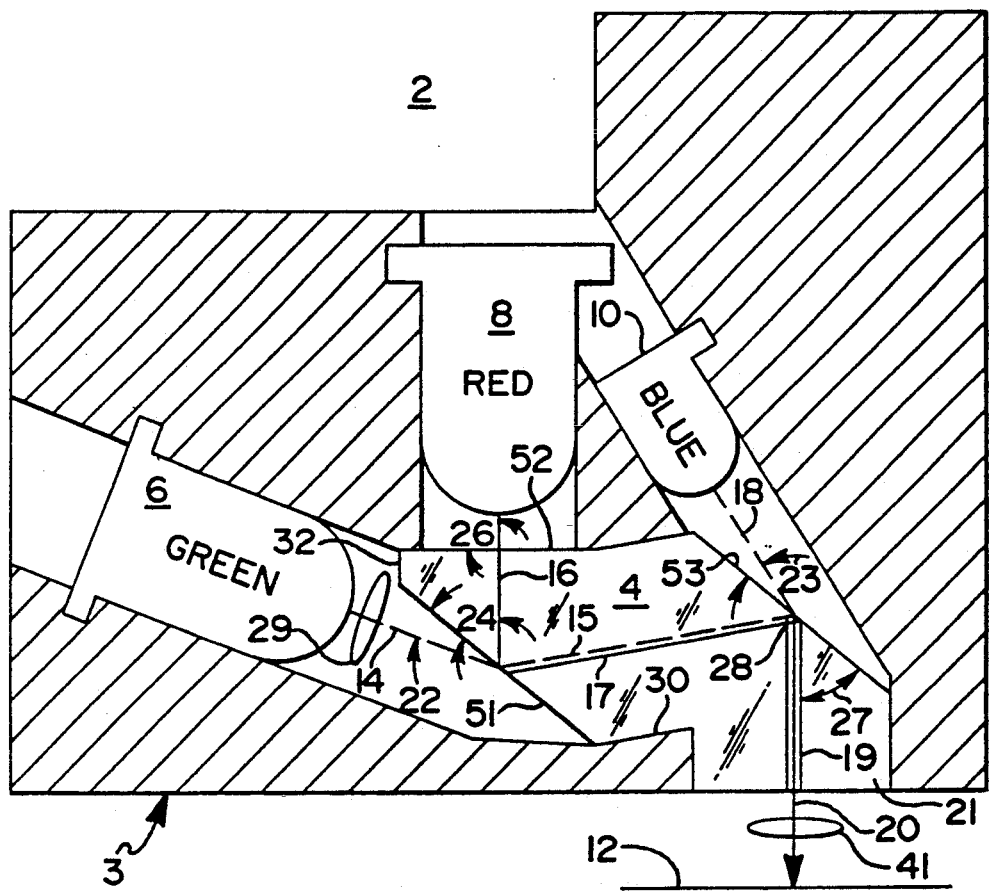
FIG. 1 is a cross-sectional view of the illumination source of the present invention.

Referring to FIG. 1, an illumination source 2 is illustrated which, in its intended application, is to provide a light having the proper mixture of green, red, and blue light to an object whose color is to be measured where the three colors of light exit the illumination source 2 at the same angle and are directed towards the object. The mounting block 3 serves to position the green LED 6, the red LED 8 and blue LED 10 so that the green light 14, the red light 16, and the blue light 18 (the major axis of which is represented by the numbered lines) from each of the respective LEDs 6, 8, and 10 are properly directed towards a lightpipe 4 which can be made of a transparent material such as Lexan polycarbonate or an acrylic which is also mounted in the mounting block 3. Also shown is the target 12 which is an object whose color is to be measured where the output light 20 that is emitted from the lightpipe 4 and illuminates the target 12 is a combination of the green light 14, red light 16, and the blue light 18.

The green LED 6 emits a light having a wavelength of approximately 555 nanometers such as that produced by the Stanley Electric Co., Ltd. as Hi-Superbright LED Pure Green 555, Part No. HBG5066X which is generated and reflected within the green LED 6 and emitted out of the green LED 6 as green light 14. The green light 14 strikes the surface S1 of the lightpipe 4 at an angle known as the green incidence angle 22 such that part of the green light 14 is reflected off of the surface S1 (not shown and lost) and part of the green light 14 is refracted. The refracted green light 15 travels through the lightpipe 4 striking surface S3 at the common transmission point 28 where it is internally reflected and exits the face of the illumination source 2 at the output section 21 of lightpipe 4 as part of output light 20.

In a like manner, the red LED 8 generates an output light having a wavelength of approximately 605 nanometers such as that produced by the Stanley Electric Co., Ltd. as Hi-Superbright LED Orange (Red) 605, Part No. HAA5066X where the light is emitted as red light 16 which strikes surface S2 of lightpipe 4 at approximately a red incidence angle 26 of 90° where the light is then reflected off of surface S1 and directed to surface S3 striking surface S3 at the common transmission point 28 approximately the same as that of the blue light 18 and the green light 14. The red light 16 then reflected and exits the illumination source 2 at output section 21 as output light 20. The major axis of red light 16 is parallel to the major axis of coaxial output light 20 as it is emitted off common transmission point 28.

In a similar manner, the blue LED 10 generates a blue light 18 having a wavelength of 470 nanometers such as that produced by CREE Research as Blue 470 where the blue light 18 strikes surface S3 at the blue incidence angle 23 at common transmission point 28 where part of the blue light 18 is reflected and lost (not shown) and the balance of blue light 18 is refracted as refracted blue light 19 which combines with the refracted and reflected green light 15 and the reflected red light 17 to produce the output light 20 which exit the lightpipe 4 at the output section 21 at substantially the same angle and strike the target 12 whose color is to be measured. In general, for any of the LEDs the reflected light that does not enter the lightpipe 4 is lost.

Surface S1, surface S2 and surface S3 can be polished flat as shown in FIG. 1. Surface angles 24, 27 and red incidence angle 26 define the angle of the surfaces S1, S2 and S3 respectively relative to the axis of the coaxial output light 20 where the axis of the red light 16 is parallel to the axis of the coaxial output light 20. To improve the collimation of light, a lens can be inserted between LED 6, 8 or 10 and the respective surface S1, S2 and/or S3 which will also improve the refractive mixing where one focusing lens 29 is shown to focus the green LED 6.

The mounting block 3 is made of an opaque material such as aluminum or a plastic material such as PVC where the lightpipe 4 can be fabricated from an acrylic plastic or a Lexan polycarbonate or other type of plastic which has the requisite reflective and refractive properties. The lightpipe 4 is approximately 0.25 inches wide (FIG. 1 is a side view) with parallel sides and surfaces S1, S2 and S3 are all perpendicular to the sides and polished. The output light 20 is emitted from the lightpipe output section 21 and has a rectangular output shape having the dimensions of approximately 0.25 inches × 0.125 inches.

The output light 20 is mixed where the refracted green light 15 and the reflected red light 17 and the refracted blue light 19 are combined and substantially mixed where the output light 20 is white in the center with stripes of the three lights recognizable around the white center. If improved mixing is desired, the lightpipe output section 21 can be extended along the axis of the output light 20 which would promote mixing and minimize the colored stripes.

An important aspect of the design of the present invention is the amount of light power that is transmitted and/or refracted and/or reflected at surface S1, at surface S2, and at surface S3. Considering the red light 16 emitted from the red LED 8, approximately 70% of the light power output is lost upon reflection off of surface S1 and another approximately 70% of the light power is lost upon the second reflection at the common transmission point 28. Considering the green light 14 emitted from the green LED 6, approximately 30% of the light power output is lost upon refraction by surface S1 and another approximately 70% of the light power is lost upon reflection off the common transmission point 28. The blue light 18 emitted from the blue LED 10 is refracted by surface S3 at the common transmission point 28 where approximately 30% of the light power output is lost. All losses are approximate since there are additional losses due to the absorption of light in the lightpipe and due to reflection off of the side.

The red LED 8 has the greatest output light power and is attenuated to the greatest degree and the next highest light output from the green LED 6 is attenuated to a lesser degree and the weakest light output from the blue LED 10 is attenuated a minimal amount. In this manner, the present invention balances the green light 14, the red light 16 and the blue light 18 light power so that the relative power between them is approximately the same so that the output light 20 has the proper color characteristics permitting an accurate color measurement to be made. Also, the proper illumination calibration is accomplished giving a balanced light power output for the desired color measurement when a Kodak White Card is used as target 12.

It is undesirable for the green light 14 or the red light 16 to impinge directly from the LED through surface S1 or surface S2 directly to the lightpipe output section 21. The mounting block 3 contains a blocking ledge 30 which serves to block the green light 14 that is emitted from directly reaching the lightpipe output section 21. Also, the red LED 8 is positioned within the mounting block 3 such that the light emitted cannot directly reach the lightpipe output section 21 but must be reflected at surface S1 and surface S3 as previously disclosed.

Now referring to FIG. 2, an elevational view of the illumination source 2 is shown mounted directly to a receiving lightpipe 34 which is joined to a light detector 36. The illumination source 2 transmits an output light 20 which strikes the target 12 and is reflected as reflected light 32 which is directed into the receiving lightpipe 34. The receiving lightpipe 34 then carries the reflected light 32 to a photo sensitive light detector 36 which can consist of a PIN photo sensitive diode where its output signal is processed by the control and processing system 37. The control and processing system 37 can perform a number of functions such as supplying power to the illumination source 2 and the light detector 36, controlling the LEDs 6, 8 and 10 by pulsing or controlling the input current to compensate for output changes with temperature, interpreting the output signal from the light detector 36 and outputting an electrical signal on line 56 which represents the measured color of the target 12. The receiving lightpipe 34 can be made of an acrylic plastic wrapped in a reflective mylar film. Other materials can serve as a lightpipe material such as Lexan.

It is contemplated that a suitable function and output indicator will be provided as well as an appropriate source of power for all of the components. For the sake of simplicity, a number of above described incidental or peripheral circuit elements are not described in detail herein, it being understood that such functions are well understood by those of ordinary skill in the art and that suitable componentry is commercially available. Thus, the reflected light 32 can be processed similar to that disclosed in application U.S. Ser. No. 07/674,247, filed on Mar. 20, 1991, the disclosure of which is hereby incorporated by reference.

The LEDs 6, 8, and 10 can be driven by a power and logic circuit within the control and processing system 37 where the LEDs 6, 8, and 10 can be simultaneously illuminated or illuminated sequentially in a rapid fashion with the detector measuring the amplitude of the reflected light 32 and then combining the measured reflected light 32 after each of the separate LEDs 6, 8, and 10 are powered. A method of using sequentially illuminated green, red, and blue LEDs to measure the color of an object is disclosed in U.S. Pat. No. 5,021,645, the disclosure of which is hereby incorporated by reference. The operation of the light detector 36 is disclosed in applications U.S. Ser. No. 07/727,730 and U.S. Ser. No. 07/674,247 and comprises any commercially available photo detector such as a PIN type Photodiode available from Hamamatsu as Part No. S1223-01.

In FIG. 2, an elevational view of the illumination source 2 of FIG. 1 is shown mounted to the receiving lightpipe 34. To better focus the output of the illumination source 2, an optic lens 41 can be mounted so as to be interposed between the illumination source 2 and the target 12 where the output light 20 passes through the lens thereby focusing the output light 20 on the target 12.

Figure 3A:
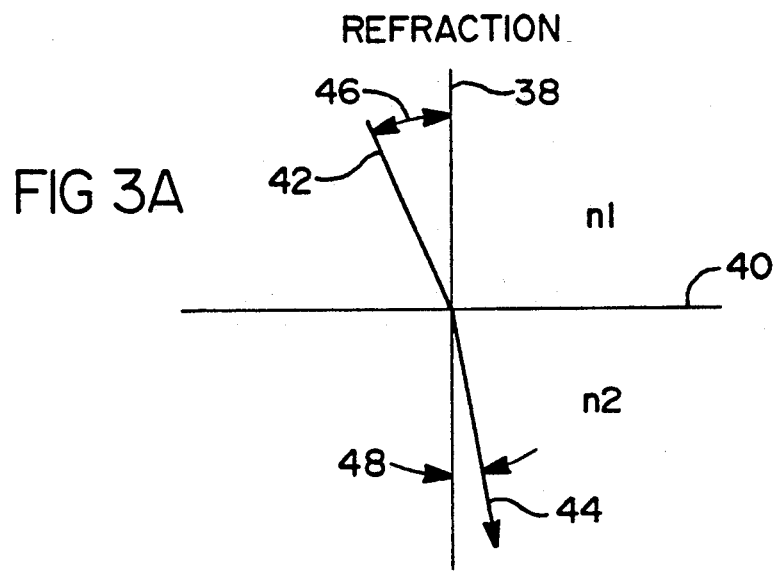
FIG. 3A is an illustration of the effect of a beam of light impinging on the lightpipe of the present invention showing a refraction effect.

FIG. 3A illustrates the physical phenomenon of refraction where emitted light 42 passes through a medium such as air having an index of refraction n1 strikes the surface of a second medium such as the lightpipe 4 having an index of refraction n2 where the angle of the emitted light 42 relative to a Y axis 38 is shown as incident angle 46 where upon reaching the surface of the medium having an index of refraction n2 shown by X axis 40, the emitted light 42 is bent so that it forms a new angle with the Y axis 38 as shown by refracted angle 48.

Figure 3B:
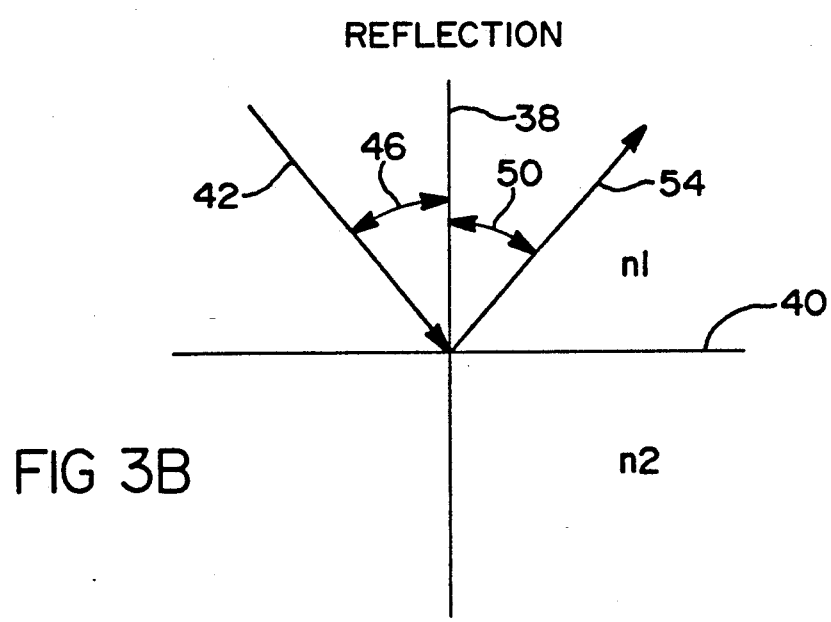
FIG. 3B is an illustration of a beam of light impinging on the lightpipe of the present invention where the light is reflected.

In a similar fashion, the FIG. 3B shows the physical phenomenon of reflection where the emitted light 42 travelling through air having an index of fraction of n1 strikes the surface of the lightpipe 4 as represented by the X axis 40 at an incident angle 46 from the Y axis 38 and the reflective wave exits at reflected angle 50 from the surface as shown by reflected wave 54. The incident angle 46 is equal in magnitude to the reflected angle 50.

The index of refraction n1 for air and the index of refraction of the lightpipe n2 both vary slightly in value with the wavelength of the incident light. Thus, the design of the lightpipe 4 depends on the light output power and wavelength of the green LED 6 and the red LED 8, and the blue LED 10 and also on the index of refraction n1 of air and the index of refraction n2 of the material that is used in the construction of the lightpipe 4. In designing the specific angle of surface S1, surface S2 and surface S3 relative to the LEDs 6, 8, and 10 and to one another, the following refraction equations is useful:

$$n1(\lambda) \sin \alpha = n2(\lambda) \sin \beta$$

where
 $\alpha$ = incident angle 46
 $\beta$ = refracted angle 48
 $\lambda$ = light wavelength
and for reflection:

$$\alpha = \theta$$

where
 $\theta$ = reflected angle 50.

Using these equations based on Snell's Law, the angle of the particular LED relative to surface S1, S2, or S3 can be calculated to ensure that the major axis of the light emitted from the LED is reflected and/or refracted so as to strike surface S3 at the common transmission point 28 and exit the lightpipe 4 coaxially with the other light waves. Likewise, the angles of surfaces S1, S2 and S3 can be calculated to achieve the desired result.

Thus, using the following components and materials based on the above equation, the specific geometry for the lightpipe 4 is as follows:

| | | |
|---|---|---|
| width = | .25 inches | *green incidence angle 22 = 19° |
| height = | 0.335 inches | *red incidence angle 24 = 90° |
| length = | 0.625 inches | *blue incidence angle 26 = 20° |
| material = | acrylic plastic | **surface S1 angle 24 = 50.6° |
| | | **surface S2 angle 26 = 90° |
| | | **surface S3 angle 27 = 51.2° |

*referenced to the surface
**referenced to the axis of output light 20

Figure 4:
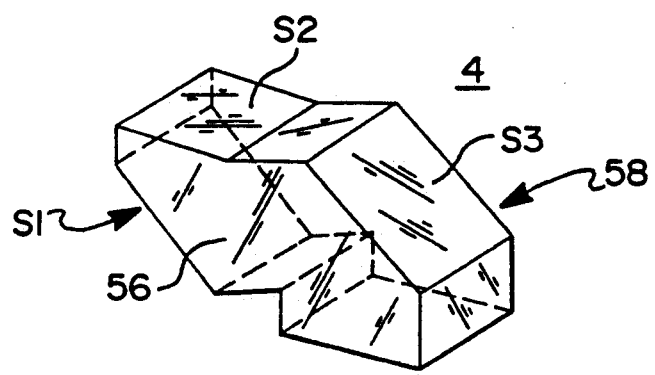
FIG. 4 is an isometric view of the lightpipe of the present invention.

FIG. 4 shows an isometric view of lightpipe 4 with surfaces S1, S2 and S3 where the sides 56 and 58 are parallel although other geometric shapes can be used.

The description above refers to particular embodiments of the present invention, it will be understood many modifications may be made without departing from the spirit thereof. The accompanying claims are intended to cover such modifications as that falls into the scope and spirit of the present invention.

The presently disclosed embodiments are therefore to be considered in all respects as illustrative and not restrictive, the scope of the invention being implicated by impending claims, rather than the foregoing description, and all changes which come within the meaning and range of equivalency of the claims are therefore intended to be embraced therein.

What is claimed is:

1. A color sensor light source for balancing and combining the emitted light from a plurality of light emitting diodes and then directing the combined emitted light toward an object comprising:

three light emitting sources each emitting light in a predetermined narrow range of wavelengths and each emitting light at a level of light power output;

a lightpipe having at least three surfaces formed on a one piece block structure, said emitted light from one of said light emitting sources directed toward one of said surfaces respectively;

a common transmission point on one of said surfaces from which said emitted light is transmitted along a substantially common path towards said object whose color is to be measured;

said surfaces oriented relative to said light emitting sources to reflect and refract said emitted light through said lightpipe and exiting therefrom at said common transmission point on one of said surfaces from which said emitted light is directed along a substantially common path towards said object whose color is to be measured, and where said emitted light from said light emitting source having a highest level of light power output is transmitted by one of said surfaces and then reflected from another of said surfaces and then reflected by another of said surfaces toward said common transmission point and where said emitted light from said light emitting source having an intermediate level of light power output is refracted by one of said surfaces and then reflected by another of said surfaces toward said common transmission point and where said emitted light from said light emitting source having a lowest level of light power output is refracted at one of said surfaces toward said common transmission point thereby substantially balancing the light power output from said three light emitting sources.

2. The color sensor light source of claim 1, wherein said light emitting sources are light emitting diodes.

3. The color sensor light source of claim 2, wherein said light emitting diodes are comprised of a first light emitting diode emitting light at a wavelength of approximately 605 nanometers at said highest light of light power output, and a second light emitting diode emitting light at a wavelength of approximately 555 nanometers at said intermediate level of light power output and a third light emitting diode emitting light at a wavelength of approximately 470 nanometers at said lowest level of light power output.

4. The color sensor light source of claim 3, wherein said surfaces are comprised of a first surface impinged directly upon by said emitted light from said first light emitting diode and a second surface impinged directly upon by said emitted light from said second light emitting diode and a third surface impinged directly upon by said emitted light from said third light emitting diode.

5. The color sensor light source of claim 1, wherein said lightpipe is formed of an acrylic material.

6. The color sensor light source of claim 1, wherein said lightpipe is formed of polycarbonate material.

7. The color sensor light source of claim 1, wherein a lens is interposed between each of said light emitting sources and each of said surfaces respectively.

8. The color sensor light source of claim 1, wherein a lens is interposed between said lightpipe and said object whose color is to be measured.

9. The color sensor light source of claim 1, wherein said surfaces are flat.

10. A method of balancing the light power output from three light emitting diodes in a color sensor light source comprising:

providing three light emitting diodes each emitting light in a predetermined range of wavelengths and each emitting light at a light power output level, a first light emitting diode having the highest light output power, a second light emitting diode having an intermediate light output power, and a third light emitting diode having a low light output power;

providing a lightpipe having at least three surfaces formed on a one piece block structure each of said light emitting diodes emitting light impinging upon each of said surfaces respectively;

transmitting said emitted light from said first light emitting diode through one of said surfaces into said lightpipe then reflecting said emitted light off another of said surfaces internal to said lightpipe then reflecting said emitted light off another of said surfaces exiting said lightpipe at a common point to illuminate an object whose color is to be measured;

refracting said emitted light from said second light emitting diode by one of said surfaces into said lightpipe then reflecting said emitted light off another of said surfaces exiting said lightpipe at said common point to illuminate said object whose color is to be measured;

refracting said emitted light from said third light emitting diode by one of said surfaces said emitted light then exiting said lightpipe at said common point to illuminate said object whose color is to be measured.

11. The method of balancing the light output power from three light emitting diodes as disclosed in claim 10 wherein, said first light emitting diode emits light at a wavelength of approximately 605 nanometers and where said second light emitting diodes emits light at a wavelength of approximately 555 nanometers and where said third light emitting diode emits light at a wavelength of approximately 470 nanometers.

12. The method of balancing the light output power from three light emitting diodes as disclosed in claim 10 wherein, said surfaces are comprised of a first surface and a second surface and a third surface where said emitted light from said first light emitting diode is transmitted by said first surface and then reflected by said second surface and then reflected by said third surface toward said object whose color is to be measured and where said emitted light from said second light emitting diode is refracted by said second surface and then reflected by said third surface toward said object whose color is to be measured and where said emitted light from said third light emitting diode is refracted by said third surface toward said object whose color is to be measured.

* * * * *